United States Patent [19]

Ross

[11] Patent Number: 4,642,557
[45] Date of Patent: Feb. 10, 1987

[54] METHOD OF AND APPARATUS FOR DETECTING EROSION

[75] Inventor: Bruce A. Ross, Windsor, Conn.

[73] Assignee: Combustion Engineering, Inc., Windsor, Conn.

[21] Appl. No.: 639,474

[22] Filed: Aug. 10, 1984

[51] Int. Cl.$^4$ ............................................ G01N 27/00
[52] U.S. Cl. ................... 324/71.2; 324/52; 324/425
[58] Field of Search .............. 324/71.2, 62, 51, 133, 324/65 CR, 425, 439, 444, 446; 340/652, 52 A, 52 B, 540, 603, 606; 116/208; 138/36; 73/86; 374/7

[56] References Cited

U.S. PATENT DOCUMENTS 1,426,456  8/1922  Case ................................ 116/208
3,197,724  7/1965  Marsh ............................. 324/71.2
3,357,237  12/1967  Lebel ............................ 324/71.2
4,184,145  1/1980  Fima ............................. 340/52 A

FOREIGN PATENT DOCUMENTS 56-24502  3/1981  Japan ............................ 324/71.2

Primary Examiner—Michael J. Tokar
Attorney, Agent, or Firm—Prutzman, Kalb, Chilton & Alix

[57] ABSTRACT

A predetermined amount of erosion of a material conveying conduit or the like is detected by inserting a probe in the conduit wall, from the side opposite to that subjected to the wear, to a predetermined depth. The probe comprises an insulated conductor which is in electrical contact, at the base of the blind hole, with the conduit. Wear of the conduit down to the level of the probe may be determined by periodic continuity measurements, a lack of continuity indicating that the inserted end of the probe has been exposed.

3 Claims, 2 Drawing Figures

METHOD OF AND APPARATUS FOR DETECTING EROSION

BACKGROUND OF THE INVENTION (1) Field of the Invention

The present invention relates to measurement of the degree of erosion of the wall of a material conveying conduit and particularly to the automatic detection of the need to repair or replace a portion of such a conduit or a similar member which is subject to wear. More specifically, this invention is directed to electrical sensors for use in determining the degree of erosion of a surface over which a material, and especially a granular and/or abrasive material, flows. Accordingly, the general objects of the present invention are to provide novel and improved methods and apparatus of such character.

(2) Description of the Prior Art

While not limited thereto in its utility, the present invention is particularly well-suited for use in monitoring the effects of erosion of a surface. Thus, by way of example, the present invention may find application in fuel pipe elbows through which pulverized coal is delivered to a furnace. There has, in the prior art, been no sensor available which would be suitable for use in an environment as harsh as a coal pipe elbow. Accordingly, it has been prior practice to periodically perform a manual inspection of such conduits in order to determine if the degree of erosive wear has been sufficient to warrant repair. Alternatively, repair/replacement schedules for fuel pipes have been established based upon past history. It would, of course, be highly desirable to avoid the necessity of performing a periodic, time consuming and expensive manual inspection. Observing a maintainence schedule based upon prior history has the obvious disadvantage that premature shutdown for maintenance will typically result. Restated, because of differences in materials which result in an unusually high rate of erosion, a very costly pipe failure could occur unless a very conservative maintenance schedule is adopted.

Surface wear detectors are, of course, well-known in the art. Such detectors have been proposed, and in some cases employed, to provide a warning of a severely worn brake lining. Examples of such brake lining wear detectors may be seen from U.S. Pat. Nos. 3,869,695 and 4,184,145. It has also been proposed to employ a resistance element embedded in a surface subject to wear so that the resistance element will wear with the surrounding surface. An example of such a wear sensor may be seen from published European patent application Ser. No. 0 077 206. The principal disadvantage of prior resistive-type devices is that the resistance material must be exposed to the same conditions as the surface of interest but will necessarily have a different wear rate when compared to that surface. Accordingly, inaccurate measurements will be obtained. Further, resistance-type wear sensors require the use of relatively complicated means for measuring the resistance of the sensor element and converting the resistance measurement into a percentage or other expression of wear.

SUMMARY OF THE INVENTION

The present invention overcomes the above-briefly discussed and other deficiencies and disadvantages of the prior art by providing a novel and improved technique which may be employed in sensing the degree of erosion of a surface which is exposed to a stream of abrasive material. The present invention also encompasses a unique sensor for use in the practice of this novel technique.

Apparatus in accordance with the preferred embodiment of the invention comprises a two-element probe which is mounted in an electrically conductive component which is subjected to the abrasive material stream or other wear producing influence. The probe is inserted into the component from the side opposite to that which is exposed to the wear producing influence. The probe comprises merely a passive coaxial arrangement of a conductor and a surrounding insulator. The probe is mounted so as to either protrude from or be flush with the back side, i.e., the non-eroded side, of the conduit or other component in which it is installed. The conductor and insulator are typically of equal length whereby, when installed to the desired depth, the conductor will be in contact with the material which defines the wear surface. Accordingly, a simple continuity measurement between the probe conductor and the component in which it is installed will, at the time of its installation, indicate substantially a short circuit. When the wear surface has been eroded to the point where the probe is exposed to the wear producing influence, a continuity test will reveal an open circuit, i.e., erosion of the wear surface will ultimately result in interrupting the electrical circuit between the inserted end of the probe and the component in which the probe has been installed. Restated, electrical continuity is interrupted when the surface wears down to the level of the inserted end of the probe thus indicating that the component is due for replacement.

BRIEF DESCRIPTION OF THE DRAWING

The present invention may be better understood and its numerous objects and advantages will become apparent to those skilled in the art by reference to the accompanying drawing wherein like reference numerals refer to like elements in the two FIGURES and in which.

DESCRIPTION OF THE DISCLOSED EMBODIMENT

Figure 1:
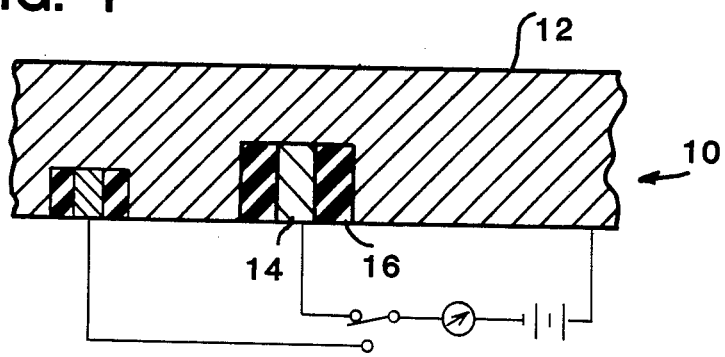
FIG. 1 is a cross-sectional, side-elevation view depicting a probe in accordance with the present invention installed in the wall of a portion of a conduit.

With reference now to the drawing, the wall of a metal conduit which is subject to erosion is indicated generally at 10, the conduit surface along which the wear producing material flows being indicated at 12. A probe in accordance with the present invention comprises a conductive pin 14 surrounded by a coaxial insulator 16.

The probe is installed in the wall of conduit 10, or some other part which is subject to erosion, to a depth that allows a preselected degree of wear to occur before the inserted end of the probe is exposed. Thus, to install the probe, a blind hole may be drilled in the outside of the conduit 10 to the appropriate depth and the probe inserted in that hole so as to place pin 14 in contact with the conductive material comprising conduit 10 at the base of the hole. The probe may be held in place by an adhesive or any other suitable means which insures that electrical contact between pin 14 and conduit 10 will be maintained even if the conduit is subject to vibration. The probe will extend to the outside of the conduit and may either be flush with the outer surface as depicted in FIG. 1 or extend outwardly beyond this outer or non-wear surface. It is, of course, possible to cut the probes to length at the installation site.

After installation of the probe a continuity test will be performed in order to insure that there is substantially a short circuit between the non-wear surface of conduit 10 and probe pin 14. Thereafter, the continuity mesurement will be periodically repeated.

Figure 2:
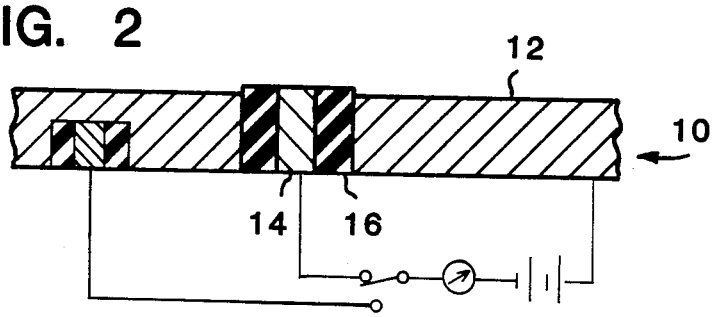
FIG. 2 is a view similar to FIG. 1 but depicting a conduit portion which has been worn to the point where replacement is required.

Referring to FIG. 2, when there has been sufficient wear of surface 12 of conduit 10 so as to expose the second or inserted end of the probe, the pin 14 will be electrically isolated from the conduit by the insulator 16. Thus, a continuity test will indicate that the circuit has "opened".

By locating the interface between the probe and conduit, i.e., the bottom of the blind hole in which the probe is installed, at the appropriate depth, it is possible to detect a need for replacement sufficiently early so as to permit scheduling of equipment shut-down, parts ordering, repair, etc. prior to the actual failure of the part in which the sensor is installed.

The continuity tests discussed above may, of course, be conducted from a remote location and under automatic control.

It is also possible to employ a plurality of the sensors of the present invention so as to permit a measurement of the degree of wear, the plural sensors being each installed at different depths in the same wear part.

It is also to be noted that the present invention is useful in indicating wear due to either friction or erosion. Thus, the present invention may be employed in such diverse applications as coal pipes and elbows, coal nozzles, mill and exhauster wear parts, boiler diagnostic systems, etc.

A wear sensor in accordance with the present invention is virtually fail proof. A sensor in accordance with the present invention is also inexpensive and extremely easy to install.

While a preferred embodiment of the present invention has been described various modifications and substitutions may be made thereto without departing from the spirit and scope of the invention. Accordingly, it is to be understood that the present invention has been described by way of illustration and not limitation.

What is claimed is:

1. A method for determining when a predetermined amount of material has been removed from the interior surface of an electrically conductive conduit which is subjected to erosive wear as a result of the passage of a solid material therethrough, the surface which is subjected to the wear being disposed oppositely with respect to an outer surface of the conduit, said method comprising the steps of:
   forming at least a first blind hole in the conduit, the blind hole extending from the outer surface toward the inner surface which is subjected to wear and having a depth commensurate with the removal of a predetermined amount of material from the inner surface;
   forming a coaxial probe having a length which is at least equal to the depth of the first blind hole, the probe comprising a conductor surrounded by an insulator;
   inserting the probe in the first blind hole until the probe conductor contacts the conduit at the base of the hole;
   performing a continuity check to insure that the probe conductor is in electrical contact with the conduit at the base of the first hole;
   securing the probe in the first hole; and
   periodically repeating the continuity check to determine when electrical contact between the probe conductor and conduit has been interrupted, a lack of continuity indicating that sufficient material has been removed from the inner surface so that the inserted end of the probe has been exposed.

2. The method of claim 1 further comprising:
   forming at least a second blind hole in the conduit, the second hole having a depth which is different from that of the first hole, the second hole extending from the outer surface toward the inner surface;
   forming a second coaxial probe having a length which is at least equal to the depth of the second hole;
   inserting the second probe in the second hole;
   performing a continuity check to insure that the conductor of the second probe is in electrical contact with the conduit at the base of the second hole;
   securing the second probe in the second hole; and
   alternating the periodic continuity checks between the first and second probes.

3. In a material conveying conduit which undergoes erosive wear, the conduit being comprised of electrically conductive material and having an outer surface and an oppositely disposed inner wear surface over which the conveyed material moves, the improvement comprising:
   at least a first blind hole in the conduit, said first hole extending from the outer surface toward the inner surface in a region of the conduit which is relatively susceptible to erosive wear, said first hole terminating at a distance from the inner surface which is commensurate with a predetermined degreee of erosion of the inner surface; and
   probe means mounted in said first hole, said probe means comprising an insulated conductor and having a length which is at least equal to the depth of said first hole, said probe means conductor being exposed at the opposite ends of said probe means, said conductor being in electrical contact with the conduit at the base of said first hole whereby the erosion of said inner surface down to the level of the base of said first hole may be determined by checking for electrical continuity between said probe conductor and the outer surface of the conduit.

* * * * *